(12) United States Patent
Buard et al.

(10) Patent No.: US 9,867,597 B1
(45) Date of Patent: Jan. 16, 2018

(54) METHOD AND SYSTEM TO NOTIFY FEMALE FERTILITY PERIOD

(71) Applicant: WITHINGS, Issy les Moulineaux (FR)

(72) Inventors: Nadine Buard, Meudon (FR); Ruiyi Yang, Coignieres (FR); Marc Besnard, Paris (FR); Cédric Hutchings, Brookline, MA (US)

(73) Assignee: WITHINGS, Issy Les Moulineaux (FR)

( * ) Notice: Subject to any disclaimer, the term of this patent is extended or adjusted under 35 U.S.C. 154(b) by 0 days.

(21) Appl. No.: 15/209,221

(22) Filed: Jul. 13, 2016

(51) Int. Cl.
| | | |
|---|---|---|
| *A61B 6/00* | (2006.01) |
| *A61B 10/00* | (2006.01) |
| *A61B 5/00* | (2006.01) |
| *A61B 5/024* | (2006.01) |
| *A61B 5/11* | (2006.01) |
| *A61B 5/0205* | (2006.01) |

(52) U.S. Cl.
CPC ........ *A61B 10/0012* (2013.01); *A61B 5/0002* (2013.01); *A61B 5/0205* (2013.01); *A61B 5/02416* (2013.01); *A61B 5/02438* (2013.01); *A61B 5/1118* (2013.01); *A61B 5/681* (2013.01); *A61B 5/743* (2013.01); *A61B 2010/0019* (2013.01); *A61B 2010/0029* (2013.01); *A61B 2562/0271* (2013.01)

(58) Field of Classification Search
CPC . A61B 10/0012; A61B 5/0002; A61B 5/0205; A61B 5/02416; A61B 5/02438; A61B 5/1118; A61B 5/681; A61B 5/743; A61B 2010/0019; A61B 2010/0029; A61B 2562/0271
See application file for complete search history.

(56) References Cited

U.S. PATENT DOCUMENTS

| | | | |
|---|---|---|---|
| 2015/0289821 A1* | 10/2015 | Rack-Gomer | G06F 3/04847 600/365 |
| 2016/0058428 A1 | 3/2016 | Shinar et al. | |
| 2016/0157717 A1* | 6/2016 | Gaster | A61B 5/0444 600/301 |

FOREIGN PATENT DOCUMENTS

| | | | |
|---|---|---|---|
| EP | 2873368 A1 | 5/2015 |
| EP | 2976998 A1 | 1/2016 |
| JP | 2006094969 A | 4/2006 |
| WO | WO 2015150434 A1 | 10/2015 |
| WO | WO 2016131630 A1 | 8/2016 |

\* cited by examiner

*Primary Examiner* — George Manuel
(74) *Attorney, Agent, or Firm* — Miller, Matthias & Hull LLP

(57) ABSTRACT

A method for determining a fertility period for a female human individual (FU), carried out in a device comprising a controller, a non-invasive heart sensor placed in contact or opposite to a portion of the skin of the individual, during the sleep of the individual, the heart sensor being configured to sense heart pulses of the individual and the controller being configured to determine the heart rate, the method comprising the following steps: /a/ collecting, at the sensor, heart pulses signals of the individual; /b/ extracting therefrom, at the controller, current heart rate during a night; /c/ calculating a minimal sleep heart rate denoted MSHR(i), over the night; /d/ comparing MSHR(i) with values of MSHR(k) recorded previously, and/or comparing MSHR(i) with a long term average of the minimal sleep heart rate values denoted LTHR; /e/ deducing therefrom a current ovulation probability index, according to a predefined criteria; /f/ if the ovulation probability index is higher than a predefined threshold denoted PTH, notify the individual with a fertility time window.

14 Claims, 4 Drawing Sheets

METHOD AND SYSTEM TO NOTIFY FEMALE FERTILITY PERIOD

FIELD OF THE DISCLOSURE

The present invention relates to methods and systems for determining a fertility period for a female human individual (FU).

BACKGROUND OF THE DISCLOSURE

There is a need to try to predict and/or notify the fertile periods of a female subject, because in some cases nowadays it may be difficult to start a pregnancy.

Many methods to predict fertile periods have been proposed, in which the female subject has to take particular measurement(s) at particular moment(s), at wakeup or during the day. However, practically, these methods prove to be annoying and discourage many.

Some have proposed to determine female menstrual cycles by measuring precisely every morning at wakeup a body core temperature of a subject. The menstrual cycle and ovulation dates are estimated by comparing the day temperature value with a monthly average reference value and/or by drafting timing charts, which often upsets the user.

Therefore, there remains a need to propose a system and a method which are particularly non-invasive and unobstrusive, and therefore well accepted by the user. Reliability and simplicity of use is also a target to meet.

SUMMARY OF THE DISCLOSURE

According to one aspect of the present invention, it is disclosed a method for determining a fertility period for a female human individual (FU), carried out in device comprising a controller, at least a non-invasive heart sensor placed in contact or opposite to a portion of the skin of the individual, at least during the sleep of the individual, the heart sensor being configured to sense heart pulses of the individual and the controller being configured to determine the heart rate ('HR'), the method comprising the following steps:

/a/ collecting, at the sensor, heart pulses signals of the individual,

/b/ extracting therefrom, at the controller, current heart rate during a daily time period of interest, said time period being comprised within a 24-hour period, /c/ calculate a minimal sleep heart rate denoted MSHR(i), over the daily time period of interest, /d/ comparing MSHR(i) with values of MSHR(k) recorded previously, and/or comparing MSHR(i) with a long term average of the minimal sleep heart rate values denoted LTHR, /e/ deducing therefrom a current ovulation probability index, according to a predefined criteria, /f/ if the ovulation probability index is higher than a predefined threshold, notify the individual with a fertility time window.

Thanks to these dispositions, the fertility time window can be notified to the user very easily, without having the need to monitor a particular biometric parameter from the user standpoint. Preferably, the user has just to wear a particular watch-like device or a specific watch at the wrist, without bothering about any particular monitoring. This proposed method proves to be unexpectedly simple to use and user-friendly.

In various embodiments of the invention, one may possibly have recourse in addition to one and/or other of the following arrangements.

According to one preferred option, the heart sensor (4) is a PhotoPlethysmoGraphic sensor, preferably placed adjacent to a portion of the skin of the individual, and at step /a/ of the method, a PhotoPlethysmoGraphy technique is used. Therefore the proposed method ensures reliability, non-invasiveness and unobstrusiveness.

According to one preferred option, the device further comprises a motion sensor (7) and the daily time period of interest is defined to be a sleep phase of the individual, the sleep phase being determined when sensed motion (sensed by the motion sensor) is below a predefined level (MTH).

It was found that performing HR filtering and analysis, particularly on sleep phases, enhances the reliability of the method.

According to one preferred option, at step /e/, the controller identifies a deep sleep phase, and the minimal sleep heart rate ('MSHR') is taken as the lowest value of heart rate during the deep sleep phase(s) of the lapsed night.

It was found that focusing especially on deep sleep phases further enhances the reliability of the method.

According to one preferred option, at step /e/, the ovulation probability index is set to exceed PTH if [MSHR(i)−MSHR(i−1)>0.75 and MSHR(i−1)−MSHR(i−2)>0.75] or if MSHR(i)−MSHR(i−3)>2.

It was found that such a substantial increase generally reflects the ovulation process.

According to one aspect, at step /e/ the ovulation probability index is set to exceed PTH if MSHR(i)−LTHR>0.1 and LTHR−MSHR(i−1)>0.1.

It was found that such event also generally reflects the ovulation process.

The ambient temperature and/or the skin temperature may also be taken into account in the calculation and/or in the predefined criteria.

One or two particular derating logic calculations can be applied to discard the effects of the ambient temperature and/or the skin temperature.

The present invention also targets a device, intended to be used to notify a female human individual (FU) with a fertility time window, comprising a controller (2) and at least a non-invasive heart sensor (4) intended to be placed in contact or opposite to a portion of the skin of the individual, at least during the sleep of the individual, the sensor being configured to sense heart pulses of the individual and the controller being configured to determine the heart rate, the controller being configured to calculate a minimal sleep heart rate denoted MSHR(i), over a daily time period of interest T(i), said time period being comprised within a 24-hour period, the controller being configured to compare MSHR(i) with values of MSHR recorded the preceding nights, and/or comparing MSHR(i) with a long term average of the minimal sleep heart rate values denoted LTHR, the controller being configured to determine a current ovulation probability index, according to a predefined criteria, and if the ovulation probability index is higher than a predefined threshold, to notify the individual with a fertility time window.

According to a preferred option, the device may further comprise a motion sensor and the daily time period of interest is defined to be a sleep phase of the individual, the sleep phase being determined when sensed motion is below a predefined level.

According to a preferred option, the heart sensor is a PhotoPlethysmoGraphic sensor, preferably placed adjacent to a portion of the skin of the individual.

In a particular embodiment, the device is a wristwatch (1) including the non-invasive sensor.

In particular embodiment, the device comprises a display element (3) to display the fertility period notification.

The present invention also targets a system, including the device as defined above and optionally a secondary sensor formed as a sensing mat in the bed (19), and/or as a video camera (18). The system may also comprise a smartphone (9) configured to display data and histograms of the female cycle assessment.

BRIEF DESCRIPTION OF THE DRAWINGS

Other features and advantages of the invention appear from the following detailed description of one of its embodiments, given by way of non-limiting example, and with reference to the accompanying drawings, in which.

DETAILED DESCRIPTION OF THE DISCLOSURE

In the figures, the same references denote identical or similar elements.

Figure 1:
FIG. 1 shows a female user sleeping and wearing a monitoring device at the wrist.
Figure 2:
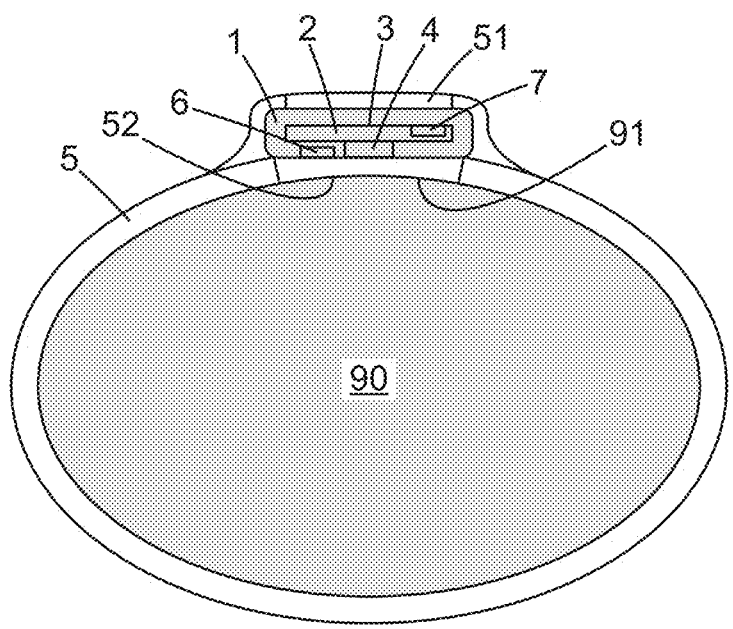
FIG. 2 shows a cross section of the monitoring device at the wrist.

As illustrated on FIGS. 1 and 2, one exemplary embodiment of the present disclosure, shown a watch-like device 1.

Advantageously, the watch-like device 1 may be worn at the wrist 90, via a wrist strap 5. Said wrist strap 5 may have a front window 51 through which user can view the display of the watch-like device and a back window 52 that will be discussed later.

The watch-like device can be a conventional wrist watch, an activity monitor otherwise called activity tracker, a smart watch, or the like.

The watch-like device 1 comprises a control unit 2 otherwise called processing unit 2 or CPU.

Figure 3:
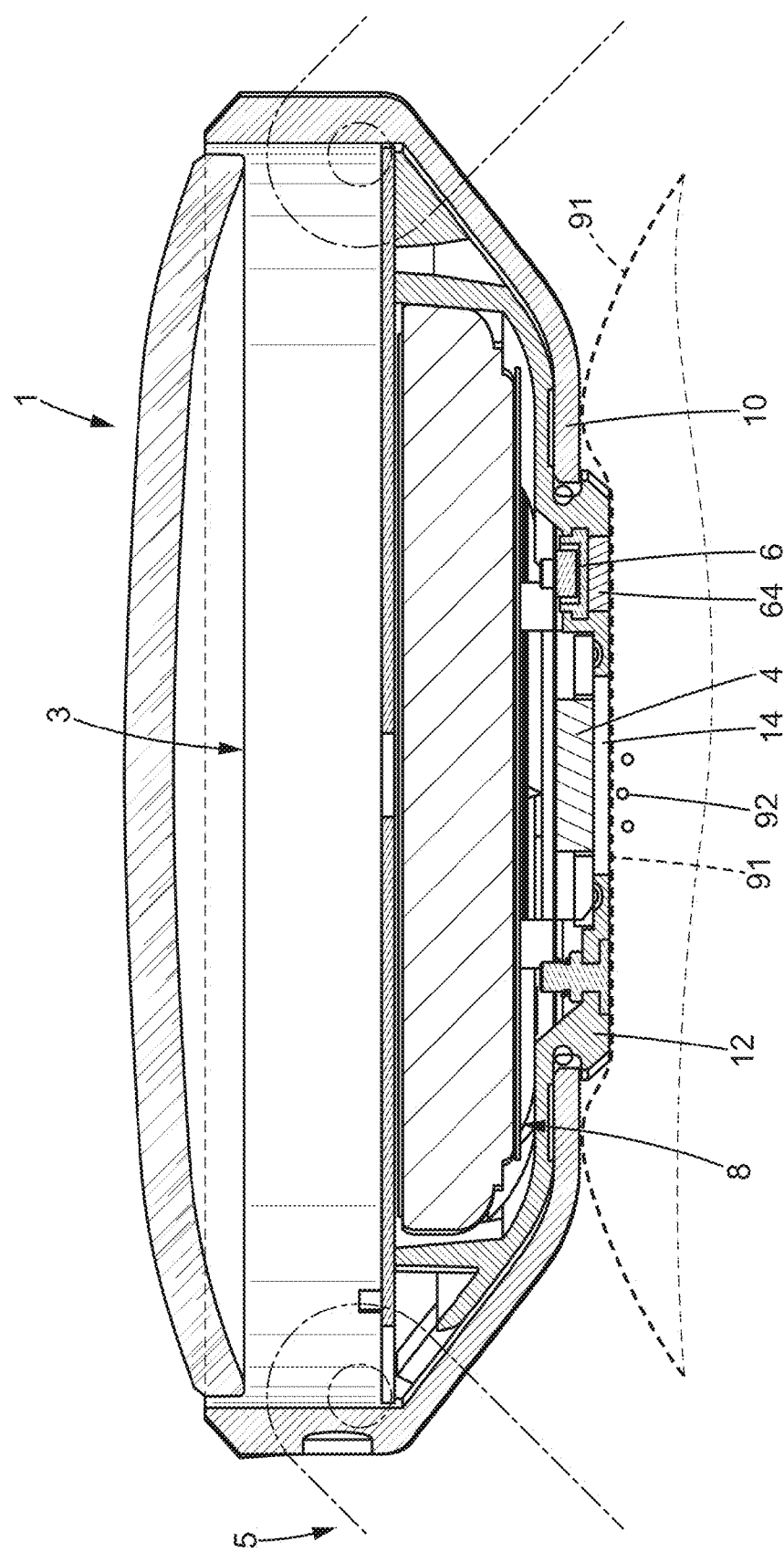
FIG. 3 shows a focused cross section of a wrist watch like embodiment.

According to the exemplified embodiment illustrated at FIG. 3, a non-invasive heart sensor 4 is placed in contact with a portion of the skin 91 of the individual, behind a protective glass 14.

Alternatively, as shown at FIG. 2, the non-invasive heart sensor 4 can be placed opposite to the skin, at a certain distance from the skin.

In a preferred embodiment, the non-invasive heart sensor 4 is a PhotoPlethysmoGraphic sensor, placed adjacent to the skin. As known per se, in one solution among others, an infrared source 41 illuminates a skin portion and a photo-receptor 40 senses the light emitted, which fluctuates in accordance with the flow of blood.

Whether the non-invasive heart sensor is in direct contact or not with the skin, it can sense the blood circulation in small capillary artery/vein network denoted 92 (FIG. 3).

However, in other embodiments, the non-invasive heart sensor 4 can be a miniaturized IR video camera using IR PhotoPlethysmoGraphic technique, contfigured to sense the heart pulses at a certain distance from the skin. A IR video camera using a IR PhotoPlethysmoGraphic technique is taught in document EP2976998 ("Baby Monitor IR").

However, in other embodiments, the non-invasive heart sensor 4 can be an impedancemetry sensor placed adjacent to the skin of the subject.

According to another variant, the non-invasive heart sensor 4 can be a ballistography sensor, like for example a sensing mat disposed within the bed, as disclosed in document EP2873368 ("sensing mat").

Additionally, a motion sensor 7 is preferably provided in the activity monitor on order to sense the accelerations and movements of the user. The motion sensor is formed in the illustrated example as a multi-axis acceleration sensor 7 (also called 'accelerometer'). The processing unit 2 samples the signals outputted by the acceleration sensors. The processing unit 2 computes said signals in order to assess user acceleration, movements and other information as this will be discussed below The activity monitor may also comprise a temperature sensor 6. In some body locations, the temperature sensor 6 is intended to be close to the body of the user in order to sense an environmental temperature close to the user's skin.

For example, as illustrated on FIG. 2, the temperature sensor 6 can be located at the back side of the device, opposite to the display 3, and thanks to the back window of the wrist strap 5, the temperature sensor is facing the skin of the user at the user's wrist 90. As illustrated on FIG. 3, the temperature sensor 6 can be arranged behind a thermally conductive cover 64.

Further, there may be provided an ambient air temperature (not shown), configured to sense the general environment temperature and which may differ from the skin temperature.

Figure 4:
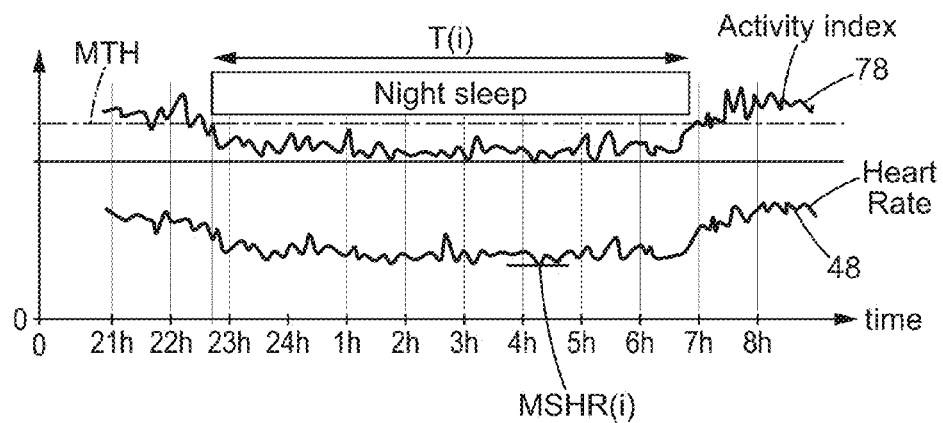
FIG. 4 is an example time chart showing a typical night sequence with determination of a Minimal Sleep Heart Rate.
Figure 5:
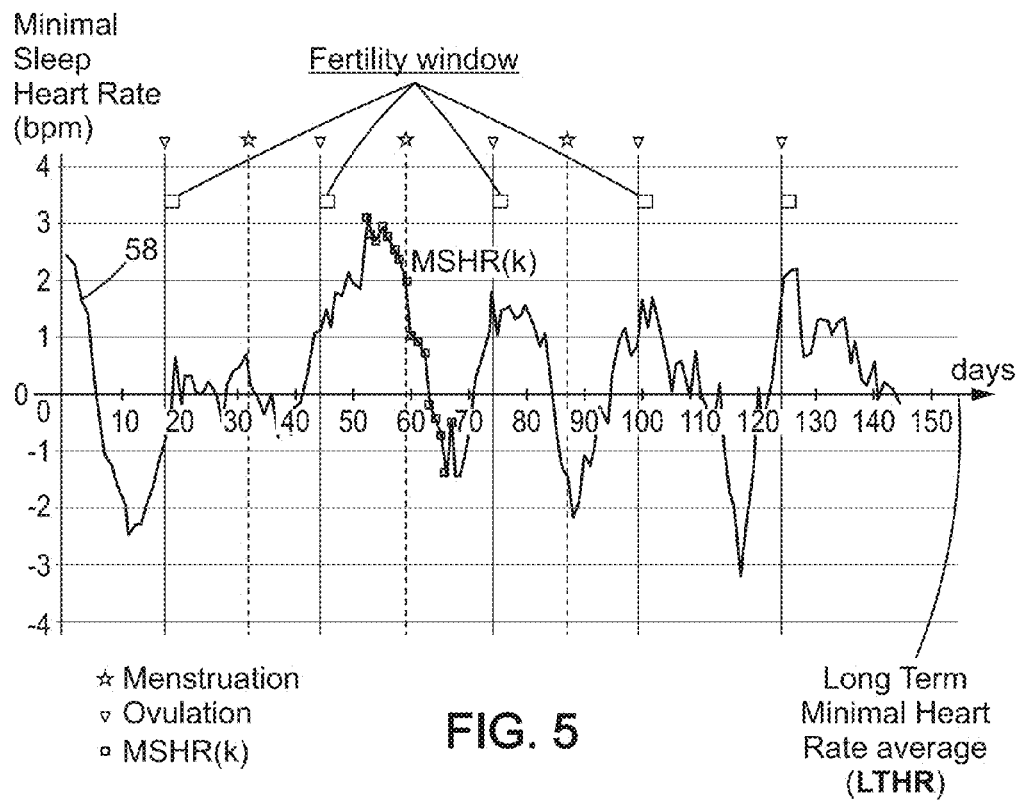
FIG. 5 shows a time chart exhibiting the Minimal Sleep Heart Rate over several ovulations cycles.
Figure 6:
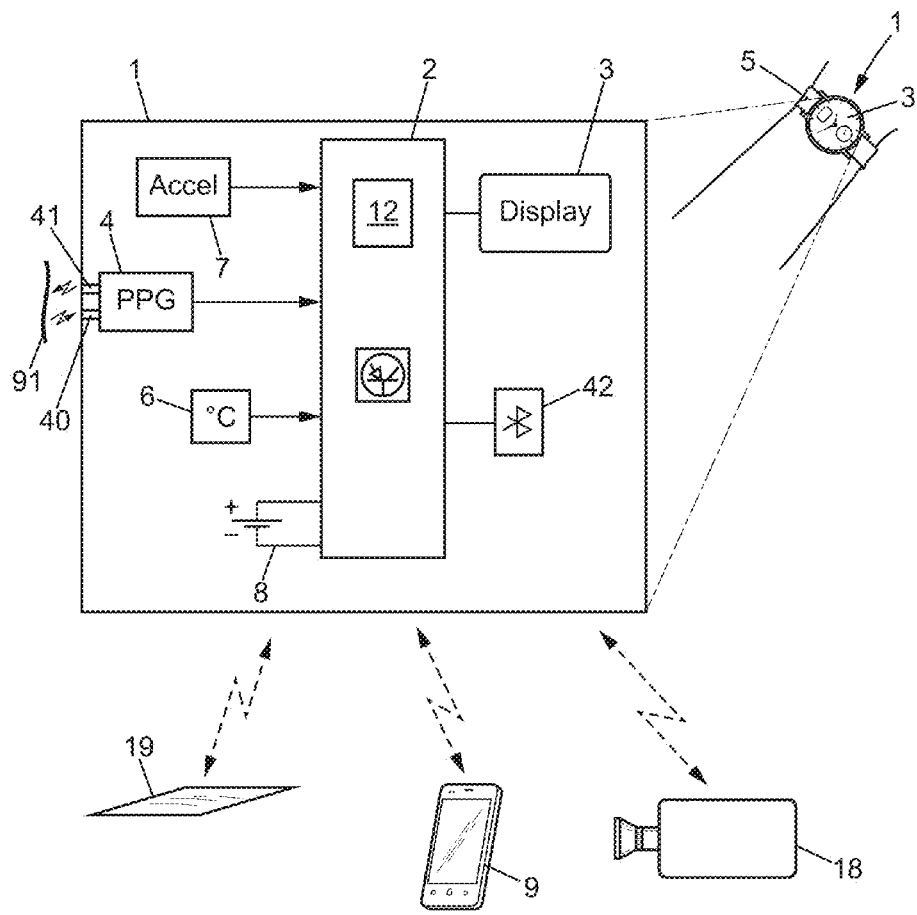
FIG. 6 shows a block diagram of the monitoring device.
Figure 7:
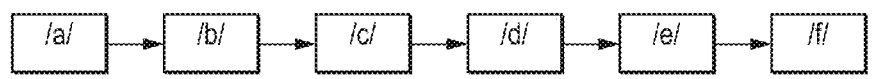
FIG. 7 illustrates the steps of the method.

As illustrated on FIGS. 4 and 5, the monitoring device 1 monitors the Heart Rate of the female subject over time. During the sleep, the heart sensor is used to sense heart pulses of the individual (step /a/ of the method), whatever the technique used (PPG, IPG, ballistography). The controller 2 is configured to determine the heart rate (HR), after measuring the time interval between two subsequent heart pulses. (step /b/ of the method). Each HR sample is recorded and this represents a curve versus time (the lower curve 48 on FIG. 4).

The heart rate (HR) is quantified in "bpm" units, i.e. beats per minute; at rest, generally an adult has a HR between 60 bpm and 80 bpm; a younger subject may have a higher range, e.g. between 70 bpm and 100 bpm.

The curve of the HR exhibits a minimum over the night. The minimal sleep heart rate over the night is denoted MSHR(i). In the shown example, this minimum occurs around 4h15.

Generally speaking, the minimum over the past 24 hours can also be considered. The minimal sleep heart rate over past 24 hours period is denoted MSHR(i), with no regard of what kind of sleep phases happened.

Focusing back to the sleep phase(s), sleep state can be determined and/or confirmed through an 'activity index' obtained from the sensed motion sensed at the motion sensor 7. As illustrated at FIG. 4, the activity index is monitored overt time (top curve 78 on FIG. 4), and such activity index is compared with a predefined level denoted MTH (for Motion Threshold). When the activity index is below MTH, then a state of sleep of FU is assumed. When the activity index turns to exceed MTH, then the state of sleep is ended. Sleep state is also assessed through the skin temperature sensor data.

There can be a low-pass filtering on the sensed motion data sensed at the motion sensor 7.

Then, on a larger time scale, each night MSHR(i) is plotted on a curve 58 shown at FIG. 5.

The controller is therefore able to compare the most recent MSHR(i) with values of MSHR(k) recorded previously. More precisely MSHR(k) recorded over the two or three previous days are of particular interest.

The controller is also able to compare the most recent MSHR(i) with a long term average of the minimal sleep heart rate values denoted LTHR. The long term average LTHR can be computed from a general HR average over a rolling window ranging on last month or last 2 months, or even more. LTHR reflects the heart rate at complete rest of an individual. This value differs from one individual to another, and therefore it's important that the calculations are referenced to this personal biometric characteristic.

Each MSHR(i) per night is recorded and this represents a curve versus time, one example denoted 58 is given at FIG. 5.

Advantageously according to the present invention, characteristics and particulars of this curve are used to detect the ovulation date of the human subject.

More precisely, the control unit is configured to perform calculation about sample points of this curve to output and ovulation probability index.

The ovulation event is declared when ovulation probability index exceeds a predefined threshold denote PTH.

More generally speaking, the controller is configured to

/e/ deduce from the curve of MSHR(i) a current ovulation probability index, according to a predefined criteria, /f/ if the ovulation probability index is higher than the threshold PTH, notify the individual with a fertility time window.

According to one option, the ovulation probability index is set to exceed PTH if [MSHR(i)−MSHR(i−1)>0.75 and MSHR(i−1)−MSHR(i−2)>0.75]. This denotes two successive increments.

According to another option, the ovulation probability index is set to exceed PTH if MSHR(i)−MSHR(i−3)>2. This denotes a general ramp-up criteria. MSHR(i)−MSHR(i−2)>1.5 is an alternate criterium.

According to another option, the ovulation probability index is set to exceed PTH if MSHR(i)−LTHR>0.1 and LTHR−MSHR(i−1)>0.1. This denotes a "zero-crossing" criteria, in other words the curve goes from negative side of LTHR to positive side of LTHR.

The watch or activity monitor 1 comprises a display 3 controlled by the processing unit 2. On the display 3, various information can be made available to the user such a particular color whenever the fertility time window number is "ON".

The monitor device comprises a wireless communication interface 42 (here for example Bluetooth™, or Bluetooth™ Low Energy 'BLE' or the like), for sending collected data to a second device 9 like a smartphone for example. Time charts, histograms and so on can be displayed in a nice fashion on the smartphone screen.

The monitor device 1 is powered by an on-board source of energy 8, for example a rechargeable battery. This battery supplies all the on-board elements in the device (the sensor 7, the display 3 and the processing unit 14, etc.). The battery can be a lithium button cell type battery, e.g. a CR2025 battery, providing an autonomy of several months in normal use.

The monitor device 1 measures continuously the user's heart rate, to determine sport/activity Heart Rate and recovery Heart Rate, daily Heart Rate, resting Heart Rate, etc. . . .

The monitor device 1 provides a 24/7 automatic activity tracker; it automatically detects and analyzes the user everyday moves, whether the user is walking, running, swimming or sleeping.

In one embodiment, the monitor device 1 is water-resistant to 50 meters (5 ATM). Regarding its mechanical construction, the wristwatch 1 illustrated at FIG. 3 comprises a stainless steel casing 10 with a diameter comprised between 32 mm and 38 mm and a thickness comprised between 10 and 14 mm, more preferably between 12 mm and 13 mm. The monitor device 1 comprises a cup-like plastic base 12 for housing the battery, the PPG sensor 4 and the temperature sensor 6.

At the system level, there can be provided beyond the already mentioned smartphone 9, a sensing mat 19 to be placed in the bed, and a conventional video camera 18. The smartphone 9 is configured to display data and histograms about the sleep and the female cycle assessment, together with one or more user notification about the abovementioned fertility time window.

The invention claimed is:

1. A method for determining a fertility period for a female human individual (FU), carried out in a device comprising a controller, one or more non-invasive heart sensor placed in contact with or opposite to a portion of the skin of the individual, at least during the sleep of the individual, the heart sensor being configured to sense heart pulses of the individual and the controller being configured to determine the heart rate, the method comprising the following steps:

/a/ receiving, from the one or more sensor, heart pulses signals of the individual, /b/ extracting therefrom, at the controller, current heart rate during a daily time period of interest T(i), said time period being comprised within a 24-hour period, /c/ calculate a minimal sleep heart rate denoted MSHR(i), over the daily time period of interest, i denoting a daily index, /d/ comparing MSHR(i) with values of MSHR(k) recorded previously, and/or comparing MSHR(i) with a long term average of the minimal sleep heart rate values denoted LTHR, /e/ deducing therefrom a current ovulation probability index, according to a predefined criteria, /f/ if the ovulation probability index is higher than a predefined threshold denoted PTH, notify the individual with a fertility time window.

2. The method of claim 1, wherein the heart sensor is a photo plethysmo graphic sensor, and at step /a/ a PhotoPlethysmoGraphy technique is used.

3. The method of claim 1, wherein the device further comprises a motion sensor and the daily time period of interest is defined to be a sleep phase of the individual, the sleep phase being determined when a sensed motion sensed by the motion sensor is below a predefined level (MTH).

4. The method of claim 3, wherein at step /c/ the controller identifies a deep sleep phase, and the minimal sleep heart rate MSHR(i) is taken as the lowest value of heart rate during the deep sleep phase(s) of the lapsed night.

5. The method of claim 1, wherein at step /e/ the ovulation probability index is set to exceed PTH if [MSHR(i)−MSHR(i−1)>0.75, and MSHR(i−1)−MSHR(i−2)>0.75], or MSHR(i)−MSHR(i−3)>2.

6. The method of claim 1, wherein at step /e/ the ovulation probability index is set to exceed PTH if MSHR(i)−LTHR>0.1 and LTHR MSHR(i−1)>0.1.

7. The method of claim 1, wherein the calculation and/or at least one predefined criteria are based on the ambient temperature and/or the skin temperature.

8. A device for notifying, intended a female human individual (FU) with a fertility time window, comprising a controller and one or more a non-invasive heart sensor intended for placement in contact with or opposite to a portion of the skin of the individual, at least during the sleep of the individual, the sensor being configured to sense heart pulses of the individual and the controller being configured to determine the heart rate, the controller being configured to calculate a minimal sleep heart rate denoted MSHR(i), over a daily time period of interest T(i), said time period being comprised within a 24-hour period, the controller being configured to compare MSHR(i) with values of MSHR recorded the preceding nights, and/or comparing MSHR(i) with a long term average of the minimal sleep heart rate values denoted LTHR, the controller being configured to determine a current ovulation probability index, according to a predefined criteria, and if the ovulation probability index is higher than a predefined threshold, to notify the individual with a fertility time window.

9. The device of claim 8, further comprising a motion sensor and with daily time period of interest is defined to be a sleep phase of the individual, the sleep phase being determined when sensed motion is below a predefined level (MTH).

10. The device of claim 8, wherein the heart sensor is a photoplethymographic sensor.

11. The device of claim 8, formed as a wristwatch including the non-invasive sensor.

12. The device of claim 8, farther comprising a display element to display the fertility period notification.

13. A system comprising a device as defined in claim 8, wherein the one or more sensor comprises a secondary sensor formed as a sensing mat in a bed, and/or as a video camera.

14. A system comprising a device as defined in claim 8, and farther comprising a smartphone configured to display data and histograms of the female cycle assessment.

* * * * *